United States Patent [19]

Park et al.

[11] Patent Number: 5,705,045
[45] Date of Patent: Jan. 6, 1998

[54] MULTI-BIOSENSOR FOR GPT AND GOT ACTIVITY

[75] Inventors: Je-Kyun Park; Kang Shin Lee, both of Seoul, Rep. of Korea

[73] Assignee: LG Electronics Inc., Seoul, Rep. of Korea

[21] Appl. No.: 703,537

[22] Filed: Aug. 27, 1996

[30] Foreign Application Priority Data

Aug. 29, 1995 [KR] Rep. of Korea ............... 27196/1995
Jan. 26, 1996 [KR] Rep. of Korea ............... 1729/1996

[51] Int. Cl.$^6$ .................................................... G01N 27/26
[52] U.S. Cl. ......................... 204/403; 204/415; 435/817; 435/287.4; 435/289.1
[58] Field of Search ........................ 204/403, 415; 435/817, 287.1, 289.1

[56] References Cited

U.S. PATENT DOCUMENTS

| | | | |
|---|---|---|---|
| 4,024,021 | 5/1977 | Stavropoulos et al. | 195/99 |
| 4,241,179 | 12/1980 | Madappally et al. | 435/16 |
| 4,271,265 | 6/1981 | Deneke et al. | 435/16 |
| 4,575,488 | 3/1986 | Krowwer et al. | 435/16 |
| 4,812,220 | 3/1989 | Iida et al. | 204/403 |
| 4,937,047 | 6/1990 | Kobayashi et al. | 436/71 |
| 5,059,526 | 10/1991 | Arai et al. | 435/17 |

Primary Examiner—Bruce F. Bell
Attorney, Agent, or Firm—John P. White

[57] ABSTRACT

Multi-biosensor in which only one enzyme is used for handy and simultaneous measurement of GPT and GOT activities, and a method for fabricating the multi-biosensor, are disclosed, the biosensor including an insulating substrate; a reference electrode formed on the insulating substrate; first and second working electrodes formed on one side of the insulating substrate having the reference electrode formed thereon; third and fourth working electrodes formed on the other side of the insulating substrate having the reference electrode formed thereon opposite to the first and second working electrodes centered on the reference electrode; first, second, third and fourth carbon paste layers formed on the first, second, third and fourth working electrodes respectively; first and second enzyme/polymer carbon paste layers formed on the first and second carbon paste layers respectively; first and second non-enzyme/polymer carbon paste layers formed on the third and fourth carbon paste layers respectively; an amino acid/polymer paste layer for making an enzymatic reaction with GPT formed extended to the first enzyme/polymer carbon paste layer and the first non-enzyme/polymer carbon paste layer; and, an amino acid/polymer paste layer for making an enzymatic reaction with GOT formed extended to the second enzyme/polymer carbon paste layer and the second non-enzyme/polymer carbon paste layer.

20 Claims, 4 Drawing Sheets

MULTI-BIOSENSOR FOR GPT AND GOT ACTIVITY

BACKGROUND OF THE INVENTION

1. Field of the Invention

The present invention relates to a biosensor for quantitative measurement of GPT(Glutamate-Pyruvate Transaminase) and GOT(Glutamate-Oxaloacetate Transaminase) activities, and more particularly, to a multi-biosensor in which only one enzyme is used for handy and simultaneous measurement of GPT and GOT activities, and a method for fabricating the multi-biosensor.

2. Discussion of the Related Art

In general, of the examination lists measured in clinic, the GPT and GOT are important enzymes which are used as indices for diagnosis of, not only hepatitis, but also damage to the liver or hepatic insufficiency. The two kinds of transaminase of GPT and GOT are also known as important enzymes, not only in diagnosis of the liver, but also in determining condition of the heart(H. U. Bergmeyer(1974). Methoden der enzymatischen Analyse, 3rd edition, Verlag Chemie, Weinheim, Volume I, pp.6–74). When the liver is damaged or in an abnormal condition, these GPT and GOT leak into blood, which are measured to obtain clinical diagnosis information.

The GPT is involved in a reaction in which an amino radical from an L-alanine which is a kind of amino acid is transferred to a 2-oxoglutarate to produce an L-glutamate and a pyruvate. And, in an inverse reaction, the L-alanine is produced. On the other hand, the GOT is involved in transferring an amino radical from an L-aspartate to a 2-oxoglutarate to alter them into an L-glutamate and an oxaloacetate, respectively.

These enzymatic reactions may be summarized as follows.

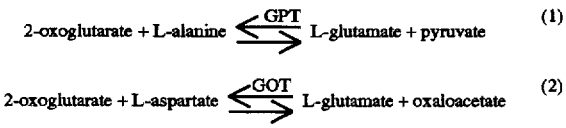

Accordingly, GPT is sometimes called as alanine transaminase(ALT), and GOT as aspartate transaminase (AST).

As disclosed in WO 91/13169, an existing method for measuring GPT and GOT uses an enzymatic reaction in which the pyruvate and oxaloacetate produced according to the reaction equation (1) and (2) are taken as substrates. Such a method has been commercialized in a form of a diagnosis kit.

That is, in case of GPT, the pyruvate produced from above reaction equation (1) reacts with a lactate dehydrogenase (LDH) to produce a lactate, in which an coeniyme of NADH(1,4-dihydronicotinamide adenine dinucleotide) is converted into NAD⁺(β-nicotinamide-adenine dinucleotide). Accordingly, since the GPT activity is proportional to an amount of pyruvate produced per minute, by measuring an amount of the NADH consumed per minute in the reaction with LDH, the amount of the GPT can be measured. In generally, this is done using an existing spectrophotometer in which the absorbance change of NADH oxidation per minute at 365 nm wavelength is measured(J. Lab. Clin. Med., 46:785–789, 1955).

On the other hand, GOT is measured using conversion of the oxaloacetate produced from the reaction equation (2) into malate in a reaction with malate dehydrogenase according to a reaction equation (4) shown below. Since the coenzyme of NADH is converted into NAD⁺ in this reaction too, the same principle of the absorbance change measurement is used.

Several biosensors using aforementioned reaction mechanism in measuring GPT and GOT have been reported. Of which one method is an example for measuring GPT using a reaction of enzyme called pyruvate oxidase in which, the pyruvate produced from reaction of equation (1) is measured by measuring the hydrogen peroxide($H_2O_2$) produced as a result of a reaction of the following reaction equation (5) or by measuring dissolved oxygen consumed in the reaction (Anal. Chim. Acta., 118:65–71, 1980).

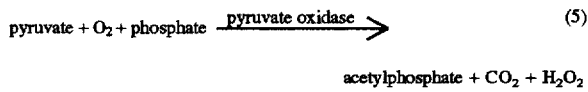

On the other hand, with regard to GOT, as oxaloacetate produces pyruvate as a result of the reaction with oxaloacetate decarboxylase as shown in the following reaction equation (6), an analysis system is reported in which GPT and GOT can be measured continuously also in association with the reaction of the reaction equation (5)(Anal. Chem., 56:1876–1880, 1984).

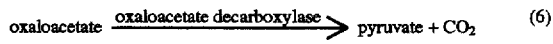

Another one example is a measuring system in which, the pyruvate oxidase is not used, but the glutamate produced in the GPT and GOT enzymatic reaction equations (1) and (2) in is used.

There is a report that a quantitative measurement of GPT or GOT can be done by measuring the amount of the hydrogen peroxide($H_2O_2$) produced in a glutamate oxidase reaction(Anal. Chim. Acta. 245:57–62, 1991).

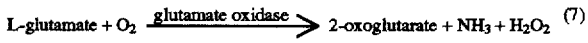

Most of present methods or devices for measuring GPT or GOT in whole blood or serum employ one of analytical methods that use spectrophotometry. As has been explained, most of current commercialized diagnosis kits use a system that measure an absorbance of the NADH which is the coenzyme involved in the reaction of lactate dehydrogenase (LDH) and malate dehydrogenase(MDH). Accordingly, those systems should be enentially provided with spectrophotometers. It is a further disadvantage of the systems that use of whole blood as a sample is difficult, and in case whole blood is used, a sample pretreatment is required.

Of the reported biosensor systems for measuring a GPT or GOT activity, in case the system uses pyruvate oxidase or glutamate oxidase reaction, a platinum electrode or dissolved oxygen electrode is applied thereto as a transducer on which an enzyme immobilized membrane is attached on the sensing portion for measuring the hydrogen peroxide($H_2O_2$) or the consumed dissolved oxygen produced as a result of the reaction of the reaction equation of (5) or (7).

In this case, there has been difficulties in miniaturization and mass production of the sensors, and the characteristics of the biosensor is dependent, not only on the enzymatic activity which is immobilized in a form of a membrane, but also sensitivity and performance of the transducer which is the base transducer. Also, since the large influence of the interferences from other electroactive species present in sample blood, accurate measurement has been difficult.

In the meantime, recent trend of the research and development puts emphasis on manufacturing the disposable biosensor. In order to manufacture the disposable biosensors, it is most important to manufacture the biosensors each of which unit elements has a consistent performance and miniaturize them at a low cost.

In case of the system which uses oxaloacetate decarboxylase reaction and pyruvate oxidase reaction for measuring GOT, since the system uses two kind of enzymes, the system has problems that, not only manufacture of the system is difficult, but also over all system becomes complicated.

In case of the measuring system which uses glutamate oxidase produced in common in the GPT and GOT enzymatic reaction equations (1) and (2), since the system has a type which forms an enzymatic immobilized membrane on an electrode, the system has problems in that the system can not overcome a limit of lifetime inherent in a bio-material, which subsequently limit continued use of the biosensor, that places a limitation on putting the system into practical use.

SUMMARY OF THE INVENTION

Accordingly, the present invention is directed to a biosensor and a method for fabricating the biosensor that substantially obviates one or more of the problems mentioned above.

An object of the present invention is to provide a biosensor and a method for fabricating the biosensor, in which only one kind of enzyme is used for handy and simultaneous measurement of GPT and GOT.

Another object of the present invention is to provide a biosensor and a method for fabricating the biosensor which can measure GPT and GOT activities accurately, which are required for an accurate diagnosis of a liver condition as well as an early stages of hepatitis.

Additional features and advantages of the invention will be set forth in the description which follows, and in part will be apparent from the description, or may be learned by practice of the invention. The objectives and other advantages of the invention will be realized and attained by the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the biosensor includes an insulating substrate, a reference electrode formed on the insulating substrate, first and second working electrodes formed on one side of the insulating substrate having the reference electrode formed thereon, third and fourth working electrodes formed on the other side of the insulating substrate having the reference electrode formed thereon opposite to the first and second working electrodes centered on the reference electrode, first, second, third and fourth carbon paste layers formed on the first, second, third and fourth working electrodes respectively, first and second enzyme/polymer carbon paste layers formed on the first and second carbon paste layers respectively, first and second non-enzyme/polymer carbon paste layers formed on the third and fourth carbon paste layers respectively, an amino acid/polymer paste layer for making an enzymatic reaction with GPT formed extended to the first enzyme/polymer carbon paste layer and the first non-enzyme/polymer carbon paste layer, and an amino acid/polymer paste layer for making an enzymatic reaction with GOT formed extended to the second enzyme/polymer carbon paste layer and the second non-enzyme/polymer carbon paste layer.

In another aspect, the present invention provides the method for fabrication biosensor, including the steps of providing an insulating substrate, forming a reference electrode on the insulating substrate, forming first and second working electrodes on one side of the insulating substrate having the reference electrode formed thereon, forming third and fourth working electrodes first and second working electrodes centered on the reference electrode, forming first, second, third and fourth carbon paste layers on the first, second, third and fourth working electrodes respectively, forming first and second enzyme/polymer carbon paste layers on the first and second carbon paste layers respectively, forming first and second non-enzyme/polymer carbon paste layers on the third and fourth carbon paste layers respectively, forming an amino acid/polymer paste layer for making an enzymatic reaction with GPT extended to the first enzyme/polymer carbon paste layer and the first non-enzyme/polymer carbon paste layer, and forming an amino acid/polymer paste layer for making an enzymatic reaction with GOT extended to the second enzyme/polymer carbon paste layer and the second non-enzyme/polymer carbon paste layer.

The insulating substrate is polymer substrate, such as of polyester, PVC, polycarbonate.

The enzyme in the enzyme/polymer carbon paste is glutamate dehydrogenase, or glutamate oxidase, and the compositions of the enzyme/polymer carbon paste layers and the non-enzyme/polymer carbon paste layers may be different depending on the kind of enzyme used therein, with consequential slight difference of the operation of the biosensor of the present invention, but others are the same.

In case glutamate oxidase is used as the enzyme, the enzyme/polymer carbon paste is formed of glutamate oxidase, hydroxyethyl cellulose and carbon powder. On the other hand, in case glutamate dehydrogenase is used as the enzyme, the enzyme/polymer carbon paste is formed of glutamate dehydrogenase, $NAD^+$, hydroxyethyl cellulose and carbon powder.

In case glutamate oxidase is used as the enzyme, the non-enzyme/polymer carbon paste is formed of bovine serum albumin, hydroxyethyl cellulose and carbon powder, in case glutamate dehydrogenase is used as the enzyme, the non-enzyme/polymer carbon paste is formed of bovine serum albumin, $NAD^+$, hydroxyethyl cellulose and carbon powder.

The amino acid/polymer paste for making an enzymatic reaction with GPT is formed of L-alanine, α-ketoglutarate and hydroxyethyl cellulose, and the amino acid/polymer paste for making an enzymatic reaction with GOT is formed of L-aspartate, α-ketoglutarate and hydroxyethyl cellulose.

The operation of the biosensor for simultaneous measurement of GPT and GOT will be explained.

As illustrated in FIGS. 1 and 2, in case glutamate oxidase is used as the enzyme of the enzyme/polymer carbon paste layer, since the glutamate produced from the two kind of enzyme reactions of GPT and GOT in common is converted into 2-oxoglutarate(or called "α- ketoglutarate") by the glutamate oxidase, and, at the same time, the oxygen dissolved in the sample is converted into hydrogen peroxide, when measuring a current change due to oxidization of the hydrogen peroxide produced by the glutamate oxidase between electrodes to which a predetermined voltage is applied, quantitative measurements of the GPT and GOT are possible at the end. It is a utilization of the fact that both the GPT and GOT enzymatic activities are proportional to the amounts of hydrogen peroxide produced per a unit time on corresponding electrodes.

On the other hand, As illustrated in FIGS. 3 and 4, in case glutamate dehydrogenase is used as the enzyme of the enzyme/polymer carbon paste layer, since the glutamate produced from the two kind of enzyme reactions of GPT and GOT in common is converted into 2-oxoglutarate(or called "α- ketoglutarate") by the glutamate dehydrogenase, and, at the same time, coenzyme of $NAD(P)^+$ is converted into NAD(P)H, when measuring a current change due to oxidization of the coenzyme of NAD(P)H into $NAD(P)^+$ between electrodes to which a predetermined voltage is applied, quantitative measurements of the GPT and GOT are possible at the end. It is a utilization of the fact that both the GPT and GOT enzymatic activities are proportional to the amounts of the NAD(P)H produced per a unit time on corresponding electrodes. However, in the present invention, the electrodes for measuring the GPT and GOT are formed on the same substrate, but separated from the other, for making the simultaneous measurement of the GPT and GOT possible according to the aforementioned principle.

Alike current sensors that uses electrochemical principle, though the biosensor of the present invention is based on 2-electrode system having a reference electrode and working electrode, the biosensor of the present invention is of a differential amplification type that has two working electrodes each. That is, in case GPT in a sample is to be measured with a biosensor which uses glutamate oxidase as the enzyme of the enzyme/polymer carbon paste layer, an oxidization reaction of the hydrogen peroxide produced by the glutamate oxidase can be detected on a working electrode to which a predetermined voltage with reference to a reference electrode is applied. And, in case GPT in a sample is to be measured with a biosensor which uses glutamate dehydrogenase as the enzyme of the enzyme/polymer carbon paste layer, an oxidization reaction of the NAD(P)H into $NAD(P)^+$ can be detected on a working electrode to which a predetermined voltage with reference to a reference electrode is applied. On the contrary, on working electrodes in which neither glutamate oxidase nor glutamate dehydrogenase is used, signals which are not relevant to the GPT reaction are detected. By detecting a signal from GPT, a quantitative measurement of a GPT is possible.

Alike the aforementioned cases, in case GOT in a sample is to be measured with a biosensor which uses glutamate oxidase as the enzyme of the enzyme/polymer carbon paste layer, an oxidization reaction of the hydrogen peroxide produced by the glutamate oxidase can be detected on a working electrode to which a predetermined voltage with reference to a reference electrode is applied. And, in case GOT in a sample is to be measured with a biosensor which uses glutamate dehydrogenase as the enzyme of the enzyme/polymer carbon paste layer, an oxidization reaction of the NAD(P)H into $NAD(P)^+$ can be detected on a working electrode to which a predetermined voltage with reference to a reference electrode is applied. On the contrary, on working electrodes in which neither glutamate oxidase nor glutamate dehydrogenase is used, signals which are not relevant to the GOT reaction are detected. By detecting a signal from GOT, a quantitative measurement of a GOT is possible.

On the other hand, since α- ketoglutarate is a substrate reactive both with GPT and GOT and producible as a result of glutamate oxidase or glutamate dehydrogenase reaction, an initial quantity of α- ketoglutarate required for reactions is made to be present excessively.

As has been explained, the biosensor of the present invention permits an accurate measurement of the GPT and GOT which can be indices for an accurate diagnosis of a liver condition and early stage of hepatitis only using one enzyme of glutamate oxidase or glutamate dehydrogenase with a method that is simpler than current measuring method.

And, as the biosensor and the method for fabricating the biosensor of the present invention allow, not only printing of the electrodes for measuring GPT and GOT on the same substrate using a current screen printing technique, but also a simultaneous differential type measurement using two working electrodes, the biosensor and the method for fabricating the biosensor can improve sensitivity significantly than current measuring method and can exclude influences from other interferences.

Moreover, the biosensor and the method for fabricating the biosensor have advantages of possible wide application to portable hepatic function measuring apparatuses and clinical automatic analyzers.

Further, since the biosensor and the method for fabricating the biosensor of the present invention permits that all of the steps of process for manufacturing the biosensor including the enzyme immobilization process can be done included in the thick film process which manufactures things using the screen printing technique, the biosensor and the method for fabricating the biosensor are favorable for miniaturization and mass production of the biosensors, and are also favorable for storage stability because the biosensors can be stored in dried condition.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the drawings.

In the drawings.

DETAILED DESCRIPTION OF THE PREFERRED EMBODIMENT

Reference will now be made in detail to the preferred embodiments of the present invention, examples of which are illustrated in the accompanying drawings.

EMBODIMENT 1. FABRICATION OF A MULTI-BIOSENSOR FOR SIMULTANEOUS MEASUREMENT OF GPT AND GOT (1) Manufacture of enzyme/polymer carbon paste and non-enzyme/polymer carbon paste A. Manufacture of enzyme/polymer carbon paste of glutamate oxidase A method for manufacturing the enzyme/polymer carbon paste is as follow.

A glutamate oxidase, (EC 1.4.3.11). extracted from streptomyces is used as the enzyme.

200 mg glutamate oxidase and 5 ml 2% hydroxyethyl cellulose put in a mortar are mixed sufficiently to make a homogeneous enzyme solution. Then, 1.3 g carbon powder is fully mixed with the enzyme solution to obtain the enzyme/polymer carbon paste, and is stored in a refrigerator for use as required in screen printing.

A method for manufacturing the non-enzyme/polymer carbon paste is as follow.

Instead of the enzyme, 200 mg bovine serum albumin and 5 ml 2% hydroxyethyl cellulose put in a mortar are mixed sufficiently to make a homogeneous non-enzyme protein solution. Then, 1.3 g carbon powder is fully mixed with the non-enzyme protein solution to obtain the non-enzyme/polymer carbon paste, and is stored in a refrigerator for use as required in screen printing.

B. Manufacture of enzyme/polymer carbon paste of glutamate dehydrogenase

A method for manufacturing the enzyme/polymer carbon paste is as follow.

A glutamate dehydrogenase, (EC 1.4.1.3). with an enzymatic activity of 23[U/mg solid] extracted from bovine liver is used as the enzyme.

200 mg glutamate dehydrogenase and 50 mg NAD$^+$($\beta$-nicotinamide-adenine dinucleotide) are put in a mortar together with 5 ml 2% hydroxyethyl cellulose, and mixed sufficiently to make a homogeneous enzyme solution. Then, 1.3 g carbon powder is fully mixed with the enzyme solution to obtain the enzyme/polymer carbon paste, and is stored in a refrigerator for use as required in screen printing.

A method for manufacturing the non-enzyme/polymer carbon paste is as follow.

Instead of the enzyme, 200 mg bovine serum albumin, 50 mg NAD$^+$ and 5 ml 2% hydroxyethyl cellulose are put in a mortar together and mixed sufficiently to make a homogeneous non-enzyme protein solution. Then, 1.3 g carbon powder is fully mixed with the non-enzyme protein solution to obtain the non-enzyme/polymer carbon paste, and is stored in a refrigerator for use as required in screen printing.

(2) Manufacture of amino acid/polymer paste

The amino acid/polymer paste for measuring GPT is manufactured by mixing 1M L-alanine and 100 mM α-ketoglutarate in 6% hydroxyethyl cellulose solution homogeneously. On the other hand, the amino acid/polymer paste for measuring GOT is manufactured by mixing 500 mM L-aspartate and 100 mM α-ketoglutarate in 6% hydroxyethyl cellulose solution homogeneously.

(3) Fabrication of a biosensor by screen printing

Figure 1:
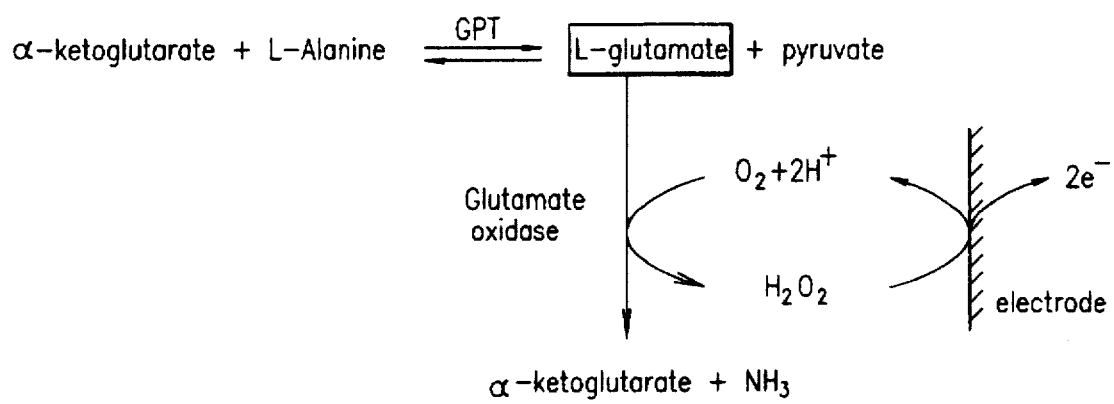
FIG. 1 illustrates enzymatic reactions by glutamate-pyruvate transaminase and glutamate-oxaloacetate transaminase in continuous form.
Figure 2:
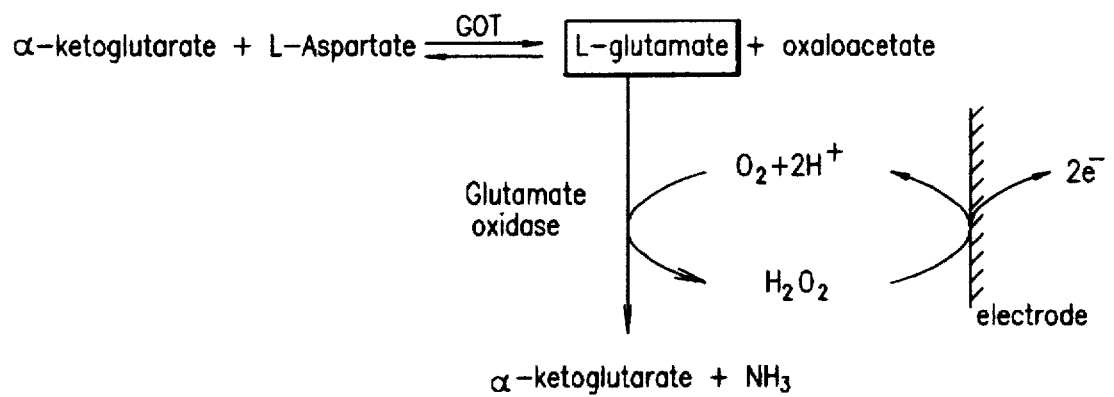
FIG. 2 illustrates enzymatic reactions by glutamate-oxaloacetate transaminase and glutamate oxidase in continuous form.
Figure 3:
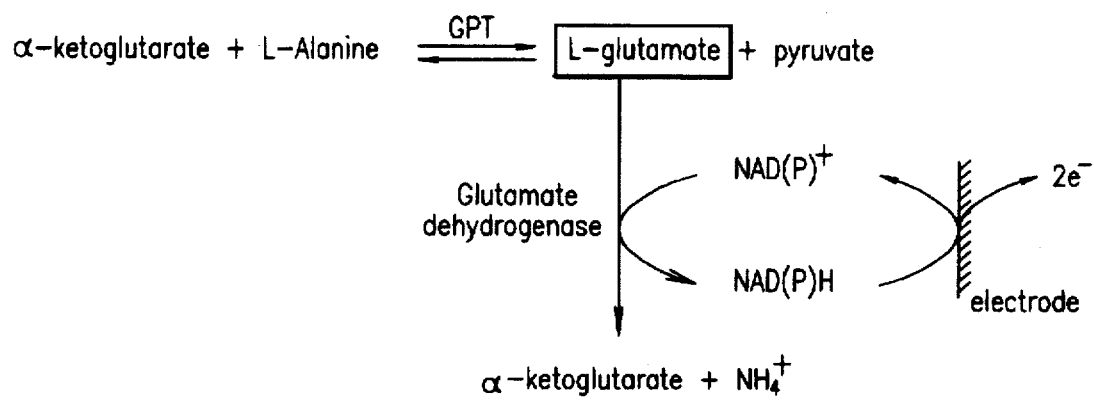
FIG. 3 illustrates enzymatic reactions by glutamate-pyruvate transaminase and glutamate-dehydrogenase in continuous form.
Figure 4:
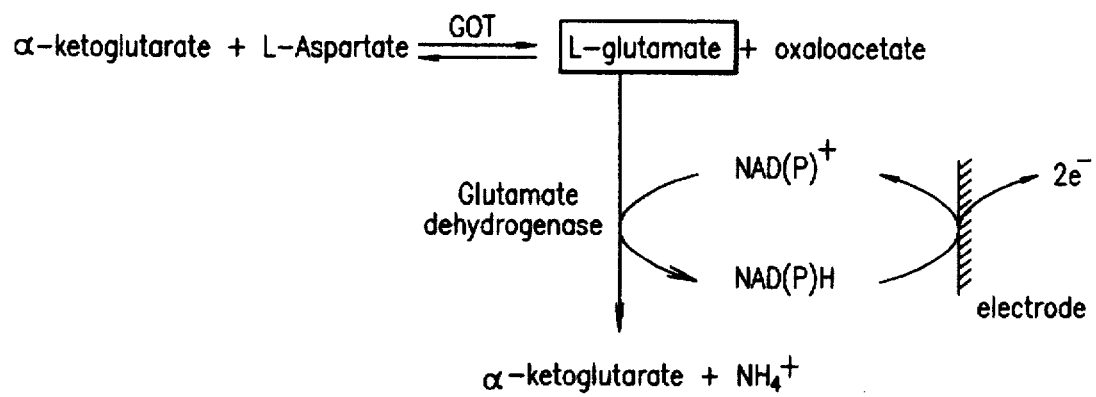
FIG. 4 illustrates enzymatic reactions by glutamate-oxaloacetate transaminase and glutamate dehydrogenase in continuous form.
Figure 5A:
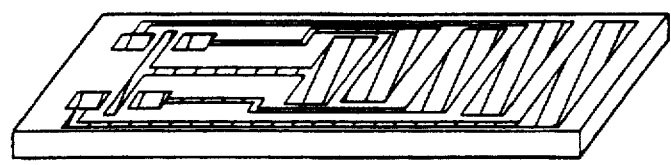
FIGS. 5a–5h illustrate plans showing the steps of a method for fabricating a biosensor in accordance with the present invention.
Figure 5B:
Figure 5C:
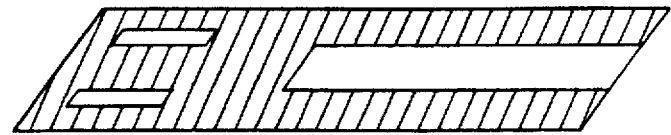
Figure 5D:

Referring to FIGS. 5a–5h and 6, a 0.3 mm thick polyester insulating substrate is cleaned with acetone, silver paste printed thereon(FIG. 5a), subjected to heat treatment under about 110 degree C. for 10 minutes, thereby to form conductive paths and connection pads. Then, carbon paste is printed on the four working electrode part of the substrate and heat treated(FIG. 5b). Next, an insulating paste is printed on an entire resultant surface of the substrate excluding the electrode part and heat treated to form an insulating film(FIG. 5c), the exposed electrode part from the insulating film is processed with 100 mM FeCl$_3$ solution for about one minute, and excessive FeCl$_3$ is washed away with distilled water, thereby an Ag/AgCl reference electrode is completed (FIG. 5d).

Figure 5E:
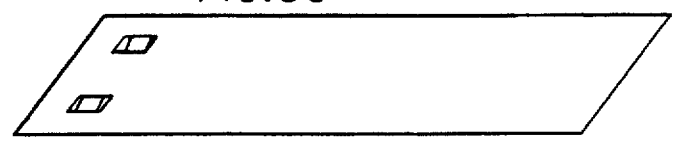
Figure 5F:
Figure 5G:
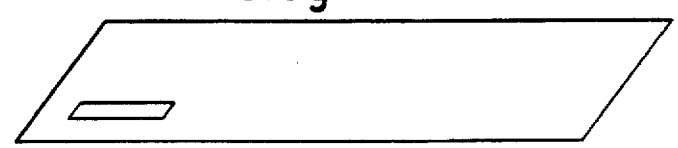
Figure 5H:
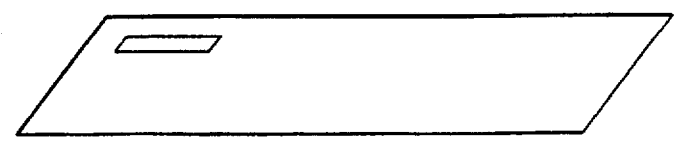
Figure 6:
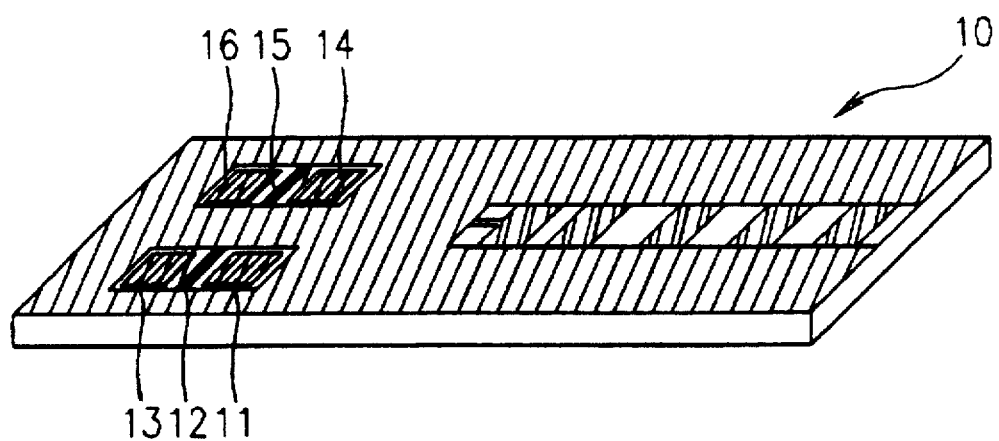
FIG. 6 is a perspective view of a biosensor in accordance with the present invention; and, FIG. 7 is a perspective view of an assistant device with which a sample for measuring GPT and GOT activities can be separated and flowed to each of enzyme activity measuring parts.

In this stage, as shown in FIGS. 5e and 5f respectively, the prepared enzyme/polymer carbon paste and non-enzyme/polymer carbon paste are printed respectively, thereby to form working electrodes for measuring GPT and GOT having glutamate oxidase or glutamate dehydrogenase respectively (13 and 16 in FIG. 6) and working electrodes for measuring GPT and GOT having no glutamate oxidase or glutamate dehydrogenase(11 and 14 in FIG. 6) respectively. Next, as shown in FIGS. 5g and 5h, polymer layers for making enzymatic reactions with GPT and GOT respectively are screen printed, thus to complete a multi-biosensor having working electrodes 11 and 13 for measuring GPT and working electrodes 14 and 16 for measuring GOT as shown in FIG. 6. As described, the multi-biosensor has reference electrodes 12 and 15 which act in common.

In this case, alike sensors which use a current electrochemical principle, though the aforementioned electrodes are based on a 2-electrode system which consists of a reference electrode 12 and a working electrode, as explained, the system is of a differential amplification type which has two working electrode each.

That is, in case GPT in a sample is to be measured with a biosensor which uses glutamate oxidase as the enzyme of the enzyme/polymer carbon paste layer, an oxidization reaction of the hydrogen peroxide produced by the glutamate oxidase can be detected on the working electrode 13 to which a predetermined voltage with reference to a reference electrode 12 is applied. And, in case GPT in a sample is to be measured with a biosensor which uses glutamate dehydrogenase as the enzyme of the enzyme/polymer carbon paste layer, an oxidization reaction of the NAD(P)H into NAD(P)$^+$ can be detected on the working electrode 13 to which a predetermined voltage with reference to a reference electrode 12 is applied. On the contrary, on the working electrodes in which neither glutamate oxidase nor glutamate dehydrogenase is used, signals which are not relevant to the GPT reaction are detected. By detecting a signal from GPT only at the end, a quantitative measurement of a GPT is possible.

Alike the aforementioned cases, in case GOT in a sample is to be measured with a biosensor which uses glutamate oxidase as the enzyme of the enzyme/polymer carbon paste layer, an oxidization reaction of the hydrogen peroxide produced by the glutamate oxidase can be detected on the working electrode 16 to which a predetermined voltage with reference to the reference electrode 15 is applied. And, in case GOT in a sample is to be measured with a biosensor which uses glutamate dehydrogenase as the enzyme of the enzyme/polymer carbon paste layer, an oxidization reaction of the NAD(P)H into NAD(P)$^+$ can be detected on the working electrode 16 to which a predetermined voltage with reference to the reference electrode 15 is applied. On the contrary, on the working electrode 14 in which neither glutamate oxidase nor glutamate dehydrogenase is used, signals which are not relevant to the GOT reaction are detected. By detecting a signal from GOT only at the end, a quantitative measurement of a GOT is possible.

(4) Formation of sample separative introduction device and completion of a biosensor.

Figure 7:
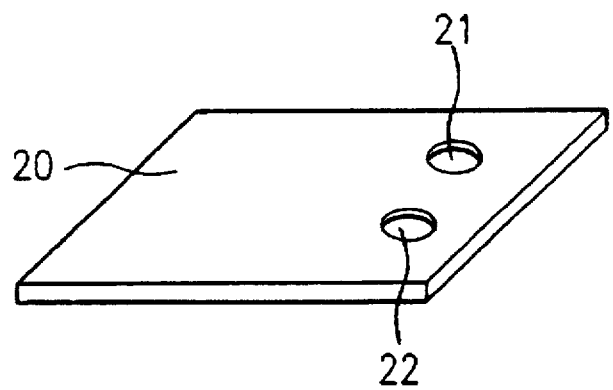
Figure 7:
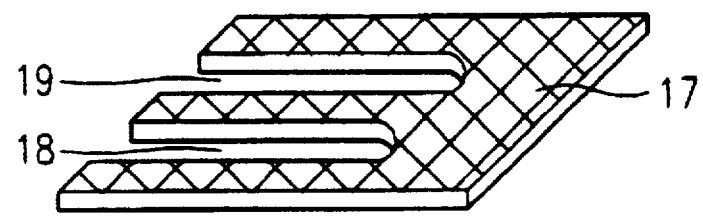

In order for the multi-biosensor thus manufactured to generate GPT and GOT signals, the biosensor should have a structure that prevents the sample from being mixed during the reactions. To this end, the biosensor of the present invention is provided with a sample separative introduction device 17 and 20 as shown in FIG. 7.

A guide layer 17 for forming grooves 18 and 19 for separation and introduction of a sample, also formed of an insulating substrate, has an adhesive material printed on both sides thereof which adhere to the electrode part and an outer protection plate 20 of insulation substrate, respectively. The openings 21 and 22 in the outer protection plate 20, accelerating a capillary tube action in the grooves, help the sample to make contact with the electrode part. The biosensors thus completed are dried at a room temperature and sealed packed individually.

It will be apparent to those skilled in the art that various modifications and variations can be made in method for fabricating semiconductor device of the present invention without departing from the spirit or scope of the invention. Thus, it is intended that the present invention cover the modifications and variations of this invention provided they come within the scope of the appended claims and their equivalents.

What is claimed is:

1. A biosensor comprising:
   an insulating substrate;
   a reference electrode formed on the insulating substrate;
   first and second working electrodes formed on one side of the insulating substrate having the reference electrode formed thereon;
   third and fourth working electrodes formed on the same plane of the insulating substrate but parallel to the first and second working electrodes centered on the reference electrode;
   first, second, third and fourth carbon paste layers formed on the first, second, third and fourth working electrodes respectively;
   first and second enzyme/polymer carbon paste layers formed on the first and second carbon paste layers respectively;
   first and second non-enzyme/polymer carbon paste layers formed on the third and fourth carbon paste layers respectively;
   an amino acid/polymer paste layer for making an enzymatic reaction with Glutamate Pyruvate Transaminase (GPT) formed covering the first enzyme/polymer carbon paste layer and the first non-enzyme/polymer carbon paste layer; and,
   an amino acid/polymer paste layer for making an enzymatic reaction with Glutamate Oxaloacetate Transaminase (GOT) formed covering the second enzyme/polymer carbon paste layer and the second non-enzyme/polymer carbon paste layer.

2. A biosensor as claimed in claim 1, wherein the insulating substrate is formed of a polymer selected from the group consisting of polyester, Polyvinyl Chloride (PVC) and polycarbonate.

3. A biosensor as claimed in claim 1, wherein each of the first and second enzyme/polymer carbon paste layers includes glutamate oxidase, hydroxyethyl cellulose and carbon powder.

4. A biosensor as claimed in claim 1, wherein each of the first and second non-enzyme/polymer carbon paste layers includes bovine serum albumin, hydroxyethyl cellulose and carbon powder.

5. A biosensor as claimed in claim 1, wherein each of the enzyme/polymer carbon paste layers includes glutamate dehydrogenase, NAD$^+$, hydroxyethyl cellulose and carbon powder.

6. A biosensor as claimed in claim 1, wherein each of the non-enzyme/polymer carbon paste layers includes bovine serum albumin, NAD$^+$, hydroxyethyl cellulose and carbon powder.

7. A biosensor as claimed in claim 1, further comprising a guide layer for forming grooves for separation and introduction of a sample, the guide layer formed for adhering both to the electrode part and an outer protection plate, the outer protection plate formed of an insulating substrate.

8. A biosensor as claimed in claim 7, wherein the electrode part includes two working electrodes for measuring GPT and two working electrodes for measuring GOT and a reference electrode.

9. A biosensor as claimed in claim 8, wherein the working electrodes for measuring GPT and the working electrodes for measuring GOT are of differential amplification types.

10. A method for fabricating a biosensor comprising the steps of:
    providing an insulating substrate;
    forming a reference electrode on the insulating substrate;
    forming first and second working electrodes on one side of the insulating substrate having the reference electrode formed thereon;
    forming third and fourth working electrodes on the same plane of the insulating film but parallel to the first and second working electrodes centered on the reference electrode;
    forming first, second, third and fourth carbon paste layers on the first, second, third and fourth working electrodes, respectively;
    forming first and second enzyme/polymer carbon paste layers on the first and second carbon paste layers, respectively;
    forming first and second non-enzyme/polymer carbon paste layers on the third and fourth carbon paste layers respectively;
    forming an amino acid/polymer paste layer for enzymatic reaction with Glutamate Pyruvate Transaminase (GPT) covering the first enzyme/polymer carbon paste layer and the first non-enzyme/polymer carbon paste layer; and,
    forming an amino acid/polymer paste layer for making an enzymatic reaction with Glutamate Oxaloacetate Transaminase (GOT) covering the second enzyme/polymer carbon paste layer and the second non-enzyme/polymer carbon paste layer.

11. A method as claimed in claim 10, wherein the insulating substrate is formed of a polymer selected from the group consisting of polyester, Polyvinyl Chloride (PVC) and polycarbonate.

12. A method as claimed in claim 10, wherein each of the first and second enzyme/polymer carbon paste layers includes glutamate oxidase, hydroxyethyl cellulose and carbon powder.

13. A method as claimed in claim 10, wherein each of the first and second non-enzyme/polymer carbon paste layers includes bovine serum albumin, hydroxyethyl cellulose and carbon powder.

14. A method as claimed in claim 10, wherein each of the enzyme/polymer carbon paste layers includes glutamate dehydrogenase, $NAD^+$, hydroxyethyl cellulose and carbon powder.

15. A method as claimed in claim 10, wherein each of the non-enzyme/polymer carbon paste layers includes bovine serum albumin, $NAD^+$, hydroxyethyl cellulose and carbon powder.

16. A method as claimed in claim 10, wherein the amino acid/polymer paste layer for making an enzymatic reaction with GPT includes L-alanine, α- ketoglutarate and hydroxyethyl cellulose.

17. A method as claimed in claim 10, wherein the amino acid/polymer paste layer for making an enzymatic reaction with GPT includes hydroxyethyl cellulose solution containing about 1M L-alanine and 100 mM α- ketoglutarate.

18. A method as claimed in claim 10, wherein the amino acid/polymer paste layer for making an enzymatic reaction with GOT includes L-aspartate, α- ketoglutarate and hydroxyethyl cellulose.

19. A method as claimed in claim 10, wherein the amino acid/polymer paste layer for making an enzymatic reaction with GOT includes hydroxyethyl cellulose solution containing about 500 mM L-aspartate and 100 mM α- ketoglutarate.

20. A method as claimed in claim 10, further comprising the step of forming a guide layer for forming grooves for separation and introduction of a sample, the guide layer formed for adhering both to the electrode part and an outer protection plate, the outer protection plate formed of an insulating substrate.

* * * * *